United States Patent [19]

Nakazawa

[11] Patent Number: 5,243,416
[45] Date of Patent: Sep. 7, 1993

[54] METHOD AND APPARATUS FOR RECORDING PLURALITY OF NON-SYNCHRONOUS IMAGE DATA

[75] Inventor: Naoyuki Nakazawa, Tokyo, Japan
[73] Assignee: Kabushiki Kaisha Toshiba, Kawasaki, Japan
[21] Appl. No.: 682,213
[22] Filed: Apr. 9, 1991
[30] Foreign Application Priority Data

Apr. 13, 1990 [JP] Japan ................................ 2-96356

[51] Int. Cl.[5] ........................... A61B 1/04; H04N 5/91
[52] U.S. Cl. ..................................... 358/98; 358/149; 358/181; 358/337
[58] Field of Search ................. 358/98, 149, 181, 337

[56] References Cited

U.S. PATENT DOCUMENTS 4,894,715 1/1990 Uchikubo .............................. 358/98

*Primary Examiner*—Howard W. Britton
*Attorney, Agent, or Firm*—Foley & Lardner

[57] ABSTRACT

Image recording method and apparatus for recording a plurality of non-synchronous image data from a plurality of imaging devices, capable of achieving a reliable image recording operation without using a plurality of time base correctors. In the apparatus, one of the non-synchronous image data from one imaging device is selectively transmitted, and a synchronous signal is extracted from that non-synchronous image data. Then, a synchronized operation command signal is obtained from an externally given operation command signal and the extracted synchronous signal, and a single time base corrector is provided for transmitting image data to be recorded in that non-synchronous image data at a predetermined recording timing, by using the synchronized operation command signal, such that the image data to be recorded transmitted by the time base corrector can be recorded.

10 Claims, 5 Drawing Sheets

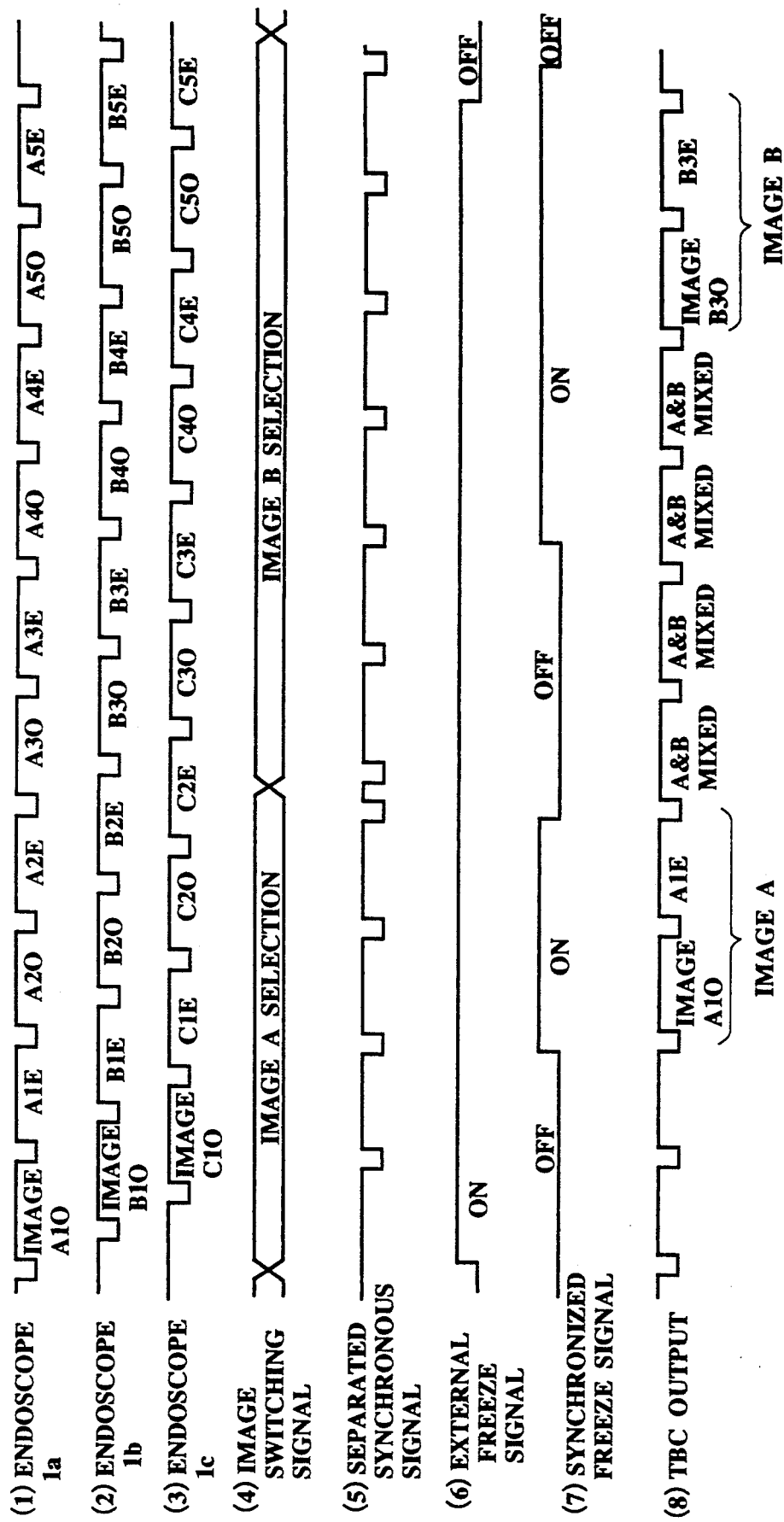

METHOD AND APPARATUS FOR RECORDING PLURALITY OF NON-SYNCHRONOUS IMAGE DATA

BACKGROUND OF THE INVENTION

1. Field of the Invention

The present invention relates to an image recording method and apparatus for recording a plurality of non-synchronous image data obtained by a plurality of imaging devices, such as endoscope devices.

2. Description of the Background Art

Recently, hospitals grow larger the number of large hospitals employing endoscope devices is also increasing. In such hospitals, image data obtained by a plurality of endoscope devices are usually recorded by a single image recording apparatus.

Now, in the very common situation in which image recording apparatus is used, if the mutually non-synchronous outputs of the plurality of the endoscope devices are simply connected to the image recording device, reliable image recording cannot be carried out because there is a possibility for the image data from more than one endoscope to get mixed up on a single recorded image.

To cope with this problem, a conventional image recording apparatus has, as shown in FIG. 1, so called time base correctors (TBC) 2a to 2c each of which is provided for each one of the plurality (three in this example) of endoscope devices 1a to 1c, where the image data from each one of the endoscope devices 1a to 1c are synchronized with an externally generated synchronous signal at each of the time base correctors 2a to 2c before being recorded. Such a conventional image recording apparatus also has an image switching device 3 for selectively transmitting one of the synchronized outputs from the time base correctors 2a to 2c to an image recording device 4 for actually recording the image data, such that the mixing up of more than one image data in a single recorded image can be prevented.

In further detail, the operation of this type of a conventional image recording apparatus will be described with reference to the timing charts of FIG. 2 to FIG. 4.

First, in the conventional image recording apparatus of FIG. 1, the endoscope devices 1a to 1c output the image data in the timings shown by (1), (2), and (3) in FIG. 2, respectively. For example, the endoscope device 1a outputs the image data for the images A1, A2, and so on obtained by its imaging operation in the timing shown by (1) where the image data contains the sequence of the odd field of an image A1 (A1O), the even field of the image A1 (A1E), the odd field of an image A2 (A2O), the even field of the image A2 (A2E), and so on, each of which is accompanied by a vertical synchronous pulse. Similarly, the endoscope device 1b outputs the image data for the images B1, B2, and so on in the timing shown by (2), while the endoscope device 1c outputs the image data for the images C1, C2, and so on in the timing shown by (3). Here, as should be clear from FIG. 2 that the vertical synchronous pulses in the image data from the endoscope devices 1a, 1b, and 1c are non-synchronous, i.e., each endoscope device is outputting the image data at its own timings not related to the output timings of the other endoscope devices.

These image data outputted from the endoscope devices 1a to 1c are subsequently synchronized with the externally given synchronous signal at each of the time base correctors 2a to 2c, so that as shown in FIG. 3, all of the vertical synchronous pulses in the outputs of the time base correctors 2a to 2c shown by (2) to (4) in FIG. 3 are synchronous to the external synchronous signal shown by (1) in FIG. 3. These synchronized outputs of the time base collectors 2a to 2c are then supplied to the image switching device 3 where an arbitrary one of the synchronized outputs from the time base collectors 2a to 2c is selectively transmitted to the image recording device 4 and recorded there.

Now, consider an exemplary case shown in FIG. 4, in which an operator using the endoscope device 1a and another operator using the endoscope device 1b simultaneously operated their respective endoscope device to generate freeze signals shown by (1) and (2) in FIG. 4 to the time base correctors 2a and 2b, so as to activate the recording of the image taken by their respective endoscope device at that point. In this case, the time base correctors 2a and 2b output the synchronized outputs for the frozen images A1 and B1 as shown by (3) and (4) in FIG. 4. Then, according to the image switching signal shown by (5) in FIG. 4, the image switching device 3 selects the image data for the image A1 from the time base correctors 2a first in order to have the image data for the image A1 recorded in the image recording device 4 as shown by (6) in FIG. 4, and then selects the image data for the image B1 from the time base correctors 2b next, in order to have the image data for the image B1 recorded in the image recording device 4 as shown by (6) in FIG. 4.

In this manner, the reliable recording of the image data from the plurality of endoscope devices has been achieved by a conventional image recording apparatus.

However, such a conventional image recording apparatus has the problem in that the time base correctors must be provided for each one of the plurality of endoscope devices involved, so that a large space is required for the image recording apparatus equipped with a plurality of time base corrector. Moreover, the time base corrector is a fairly expensive circuit device, so that the image recording apparatus becomes increasingly expensive as the number of endoscope devices increases.

SUMMARY OF THE INVENTION

It is therefore an object of the present invention to provide image recording method and apparatus for recording a plurality of non-synchronous image data from a plurality of imaging devices, capable of achieving a reliable image recording operation without using a plurality of time base correctors.

According to one aspect of the present invention there is provided an image recording apparatus for recording a plurality of non-synchronous image data from a plurality of imaging devices, comprising: means for selectively transmitting one of the non-synchronous image data from one imaging device; means for extracting synchronous signal from said one of the non-synchronous image data; means for obtaining a synchronized operation command signal from an externally given operation command signal and the extracted synchronous signal; a single time base collector means for transmitting image data to be recorded in said one of the non-synchronous image data at a predetermined recording timing, by using the synchronized operation command signal; and recording device for recording the image data to be recorded transmitted by the time base collector means.

According to another aspect of the present invention there is provided an image recording method for recording a plurality of non-synchronous image data from a plurality of imaging devices, comprising the steps of: selectively transmitting one of the non-synchronous image data from one imaging device; extracting synchronous signal from said one of the non-synchronous image data; obtaining a synchronized operation command signal from an externally given operation command signal and the extracted synchronous signal; providing a single time base corrector means for transmitting image data to be recorded in said one of the non-synchronous image data at a predetermined recording timing, by using the synchronized operation command signal; and recording the image data to be recorded transmitted by the time base corrector means.

Other features and advantages of the present invention will become apparent from the following description taken in conjunction with the accompanying drawings.

BRIEF DESCRIPTION OF THE DRAWINGS

FIG. 6 is a timing chart for a set of signals in the image recording apparatus of FIG. 5.

DETAILED DESCRIPTION OF THE PREFERRED EMBODIMENTS

Figure 1:
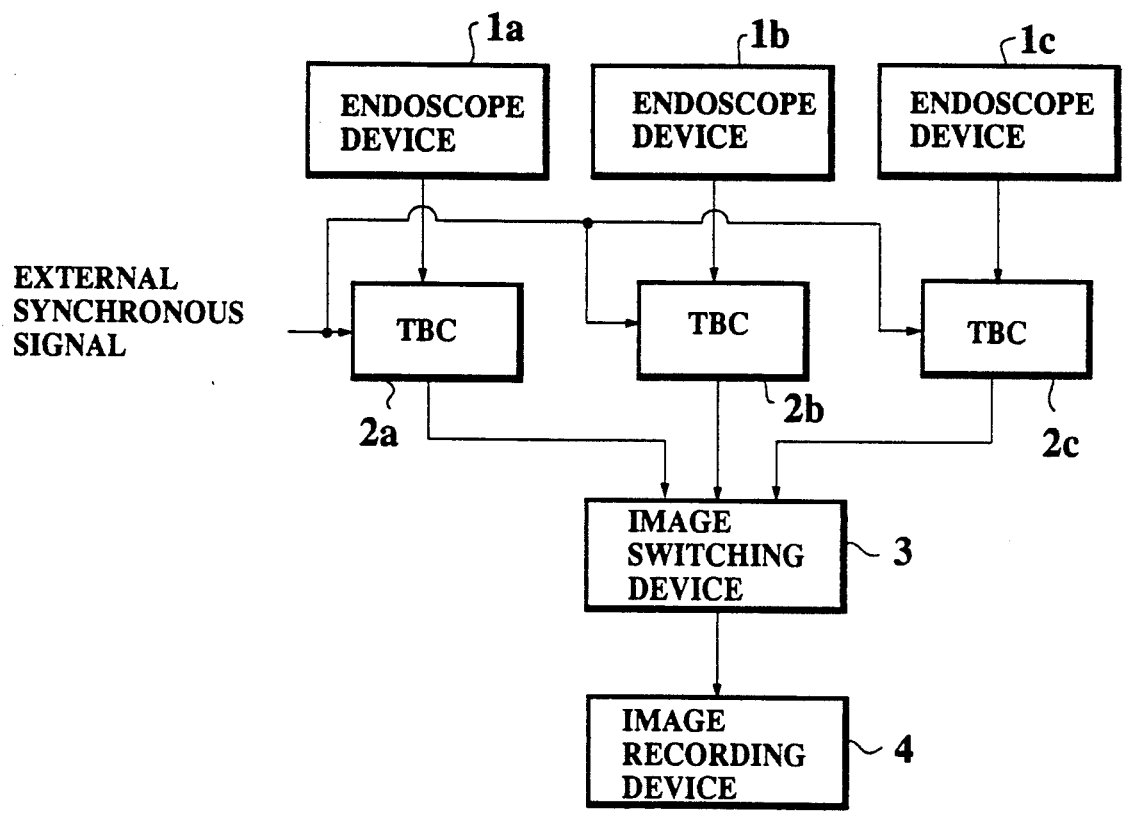
FIG. 1 is a schematic block diagram of a conventional image recording apparatus.
Figure 2:
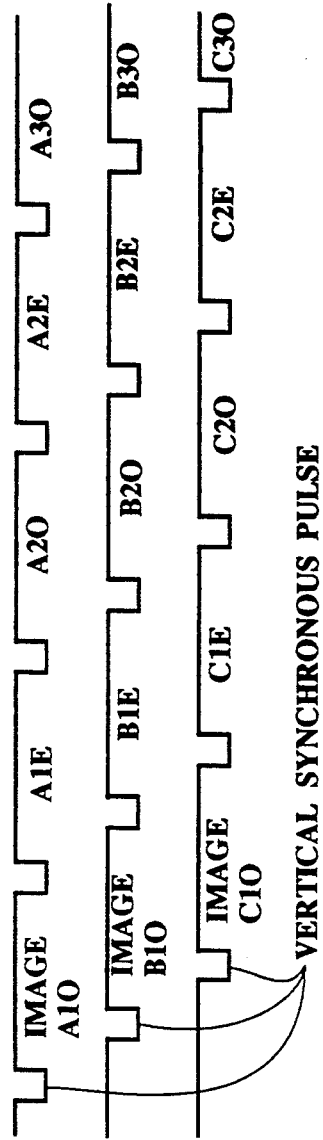
FIG. 2 is a timing chart for a set of signals in the conventional image recording apparatus of FIG. 1.
Figure 3:
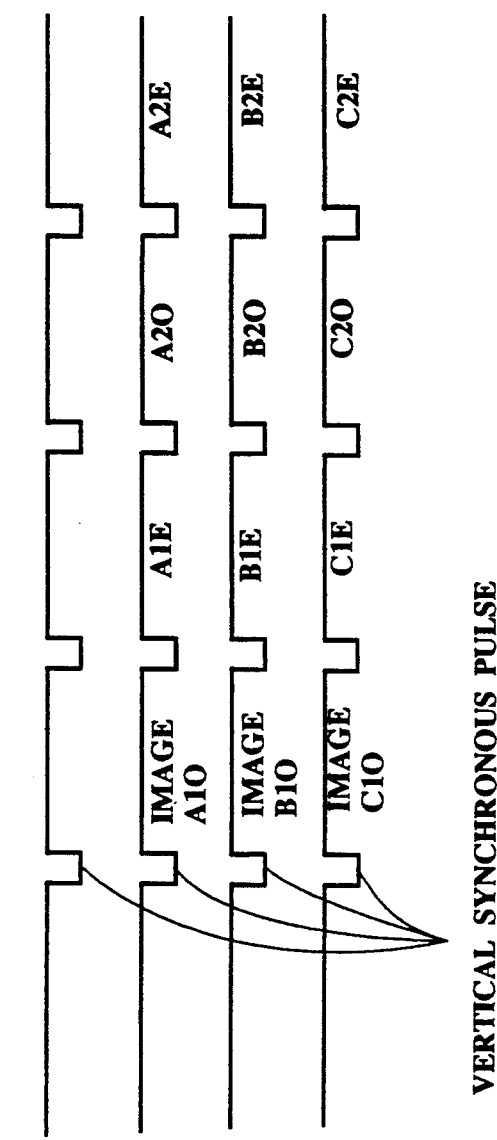
FIG. 3 is a timing chart for another set of signals in the conventional image recording apparatus of FIG. 1.
Figure 4:
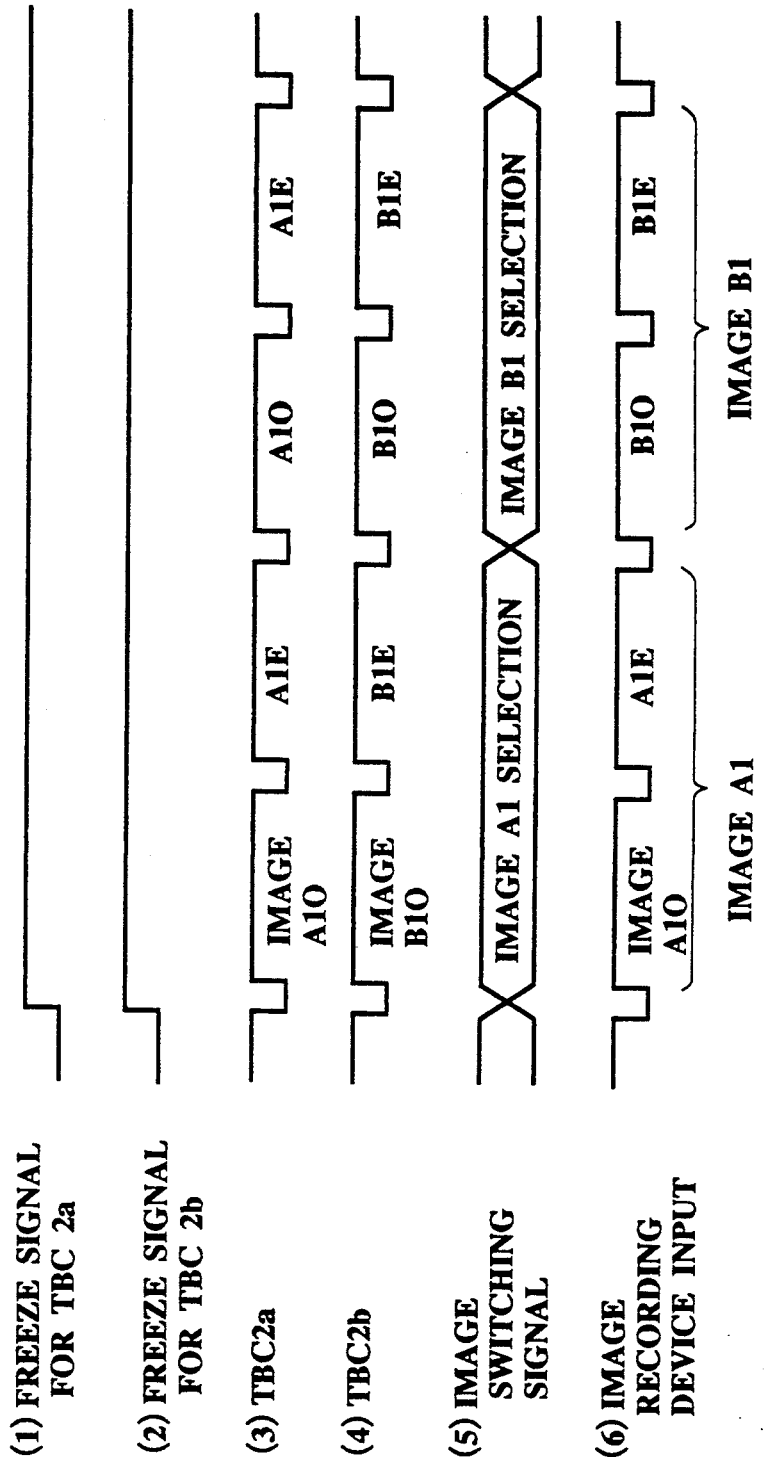
FIG. 4 is a timing chart for a still another set of signals in the conventional image recording apparatus of FIG. 1.
Figure 5:
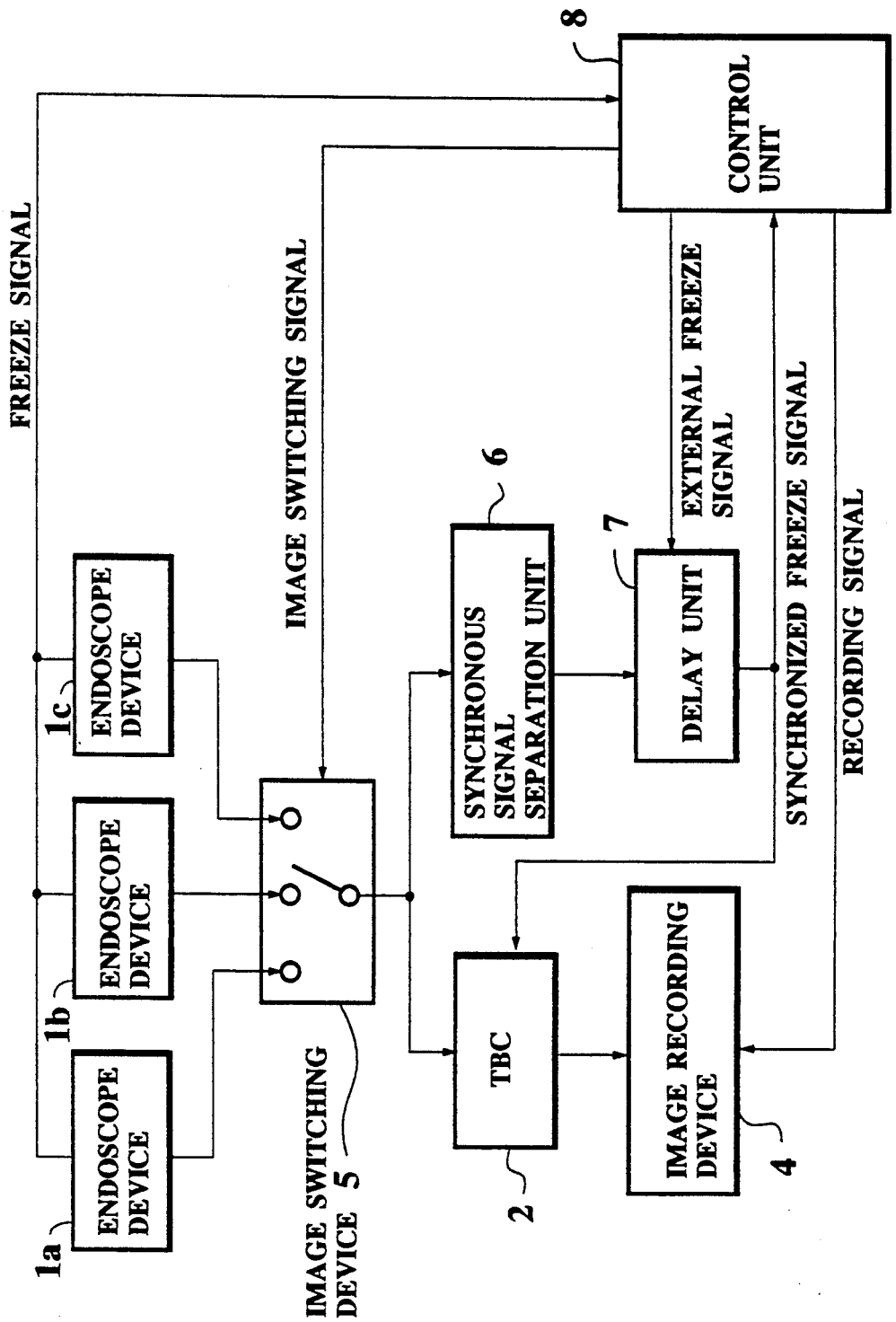
FIG. 5 is a schematic block diagram of one embodiment of an image recording apparatus according to the present invention.

Referring now to FIG. 5, one embodiment of an image recording apparatus according to the present invention will be described in detail. This embodiment of an image recording apparatus is for recording a plurality of non-synchronous image data from a plurality (three in the following description for the sake of definiteness) of endoscope devices 1a, 1b, and 1c.

This image recording apparatus comprises an image switching device 5 for selectively transmitting one of the non-synchronous image data from the endoscope devices 1a, 1b, and 1c according to an image switching signal; a time base corrector 2 for receiving the selected one of the image data selected by the image switching device 5, and outputting the image data to be recorded at the timing of the internal synchronization clock provided within the time base corrector 2 itself; an image recording device 4 for actually recording the image data to be recorded outputted from the time base corrector 2; a synchronous signal separation unit 6 for extracting the synchronous signal from the selected one of the image data selected by the image switching device 5 and then extracting a frame index signal from the extracted synchronous signal; a delay unit 7 for delaying an external freeze signal by a predetermined number of frames by using the frame index signal extracted by the synchronous signal separation unit 6 and supplying the delayed external freeze signal as the synchronized freeze signal to the time base corrector 2; and a control unit 8 for controlling the operation of the apparatus by providing the image switching signal to the image switching device 5, the external freeze signal to the delay unit 7, and a recording signal for initiating the recording operation of the image recording device 4, according to the freeze signal from the endoscope devices 1a, 1b, and 1c, and the synchronized freeze signal obtained by the delay unit 7.

Referring now to the timing chart of FIG. 6, the operation of this image recording apparatus will be described in detail.

First, as shown by (1), (2), and (3) in FIG. 6, the image data from the endoscope devices 1a, 1b, and 1c contain sequences of vertical synchronous pulses and image fields, where each image field comprises an odd field such as A1O and an even field such as A1E. In general, these image data from the endoscope devices are non-synchronous as shown in FIG. 6.

In this situation, the operator operating each endoscope device can operate a copy switch (not shown) provided on the endoscope device whenever a desired image is obtained by the endoscope device so as to output the freeze signal to the control unit 8 and have the frozen image of this desired image recorded in the image recording apparatus.

Now, consider the case in which the operators using the endoscope devices 1a and 1b simultaneously operated the copy switches on their respective endoscope devices.

In response to the freeze signals from the endoscope devices 1a and 1b, the control unit 8 produces the image switching signal for controlling the image switching device 5 to select the image data A from the endoscope device 1a first as shown by (4) in FIG. 6.

Then, the image data A from the endoscope device 1a is outputted from the image switching device 5, and the synchronous signal in the image data A is extracted by the synchronous signal separation unit 6 to obtain the separated synchronous signal shown by (5) in FIG. 6, and the frame index signal in the extracted synchronous signal is outputted to the delay unit 7.

In addition to the frame index signal from the synchronous signal separation unit 6, the delay unit 7 also receives the external freeze signal shown by (6) in FIG. 6 from the control unit 8 in correspondence to the freeze signal from the endoscope devices 1a and 1b. Here, the delay unit 7 delays the external freeze signal by a predetermined number of frames which is taken to be one frame in FIG. 6 for the sake of definiteness, so that the synchronized freeze signal shown by (7) in FIG. 6 is turned into an ON state during the second image field from the beginning of ON state in the external freeze signal. This delay by delay unit 7 has a merit of securing accurate selection of the image to be recorded. Namely, because the freeze signal may be produced at an arbitrary timing regardless of the synchronization timing of the image data from the endoscope device, so that the first frame after the beginning of the ON state in the external freeze signal may be incomplete, and the selection of such an incomplete frame can be avoided by the delaying of the delay unit 7.

Then, at the time base corrector 2, the image of a frame immediately preceding the frame specified by the ON state of the synchronized freeze signal such as an image A comprising A1O and A1E is outputted to the image recording device 4 as the image data to be recorded at the timing of the internal synchronization clock provided within the time base corrector 2 itself, as shown by (8) in FIG. 6.

Meanwhile, the recording signal from the control unit 8 is also supplied to the image recording device 4 at the timing of the image data output by the time base collector 2 such that the image A outputted from the time base collector 2 can be recorded by the image recording device 4.

Next, when the recording of the image A is completed, the synchronized freeze signal is turned into OFF state as shown by (7) in FIG. 6, and the control unit 8 produces the image switching signal for controlling the image switching device 5 to select the image data B from the endoscope device 1b next as shown by (4) in FIG. 6.

Hereafter, the process similar to that described above for the recording of the image A is performed with respect to the image B so as to have the image B recorded.

Namely, the image data B from the endoscope device 1b is outputted from the image switching device 5, and the synchronous signal in the image data B is extracted by the synchronous signal separation unit 6 to obtain the separated synchronous signal shown by (5) in FIG. 6, and the frame index signal in the extracted synchronous signal is outputted to the delay unit 7.

In addition to the frame index signal from the synchronous signal separation unit 6, the delay unit 7 also receives the external freeze signal shown by (6) in FIG. 6 from the control unit 8 in correspondence to the freeze signal from the endoscope devices 1a and 1b. Here, the delay unit 7 delays the external freeze signal by a predetermined number of frames which is taken to be one frame in FIG. 6 for the sake of definiteness, so that the synchronized freeze signal shown by (7) in FIG. 6 is turned into an ON state during the second image field from the switching to the image B.

Then, at the time base corrector 2, the image of a frame immediately preceding the frame specified by the ON state of the synchronized freeze signal such as an image B comprising B30 and B3E is outputted to the image recording device 4 as the image data to be recorded at the timing of the internal synchronization clock provided within the time base corrector 2 itself, as shown by (8) in FIG. 6.

Meanwhile, the recording signal from the control unit 8 is also supplied to the image recording device 4 at the timing of the image data output by the time base corrector 2 such that the image B outputted from the time base corrector 2 can be recorded by the image recording device 4.

In the above described operation, the actual time elapsing between the neighboring image fields in each image data is practically too short for the human eye to detect the changes in the neighboring image fields, so that even though the operators operate the copy switches for the images A1 and B1, the recorded images A1 and B3 can effectively be regarded as equivalent to the desired images A1 and B1.

Thus, according to this embodiment, it is possible to provide an image recording apparatus for a plurality of non-synchronous image data from a plurality of imaging devices, capable of achieving a reliable image recording operation without undesirable mixing of more than one images in a single recorded image while using only one time base corrector, because the image to be recorded is selected by using the synchronized freeze signal obtained from the frame index in the synchronous signal of the image data from one of the endoscope devices and the freeze signal from the same one of the endoscope device, such that the synchronization by the time base corrector for the sake of recording by the image recording device can be handled by a single time base corrector.

Accordingly, the image recording apparatus of this embodiment can be constructed in size at less cost than the conventional image recording apparatus using a plurality of time base correctors.

It is to be noted that the internal synchronization clock in the above embodiment can be replaced by an external synchronization clock without affecting the advantageous features of the present invention.

It is also to be noted that the present embodiment is equally applicable to a system using imaging devices other than the endoscope devices such as communication devices, and the command signals other than the freeze signal, recording signal, etc. used in the embodiment described above.

Besides these, many modifications and variations of the above embodiments may be made without departing from the novel and advantageous features of the present invention. Accordingly, all such modifications and variations are intended to be included within the scope of the appended claims.

What is claimed is:

1. An image recording apparatus for recording a plurality of non-synchronous image data from a plurality of imaging devices, comprising:
   means for selectively transmitting one of the non-synchronous image data from one imaging device;
   means for extracting synchronous signal from said one of the non-synchronous image data;
   means for obtaining a synchronized operation command signal from an externally given operation command signal and the extracted synchronous signal;
   a single time base corrector means for transmitting image data to be recorded in said one of the non-synchronous image data at a predetermined recording timing, by using the synchronized operation command signal; and
   a recording device for recording the image data to be recorded transmitted by the time base corrector means.

2. The image recording apparatus of claim 1, wherein the imaging devices are endoscope devices.

3. The image recording apparatus of claim 1, wherein the time base corrector means has a synchronization clock to provide the predetermined recording timing.

4. The image recording apparatus of claim 1, wherein the operation command signal is a freeze signal and a synchronized operation command signal is a synchronized freeze signal.

5. The image recording apparatus of claim 4, wherein the synchronized freeze signal indicates the image data to be recorded in said one of the non-synchronous image data.

6. An image recording method for recording a plurality of non-synchronous image data from a plurality of imaging devices, comprising the steps of:
   selectively transmitting one of the non-synchronous image data from one imaging device;
   extracting a synchronous signal from said one of the non-synchronous image data;
   obtaining a synchronized operation command signal from an externally given operation command signal and the extracted synchronous signal;

providing a single time base corrector means for transmitting image data to be recorded in said one of the non-synchronous image data at a predetermined recording timing, by using the synchronized operation command signal; and recording the image data to be recorded transmitted by the time base corrector means.

7. The image recording method of claim 6, wherein the imaging devices are endoscope devices.

8. The image recording method of claim 6, wherein the time base corrector means has a synchronization clock to provide the predetermined recording timing.

9. The image recording method of claim 6, wherein the operation command signal is a freeze signal and a synchronized operation command signal is a synchronized freeze signal.

10. The image recording method of claim 9, wherein the synchronized freeze signal indicates the image data to be recorded in said one of the non-synchronous image data.

* * * * *